United States Patent
Benz et al.

(10) Patent No.: US 10,894,111 B2
(45) Date of Patent: Jan. 19, 2021

(54) HIGH REFRACTIVE INDEX HYDROPHILIC MATERIALS

(71) Applicant: Benz Research and Development Corp., Sarasota, FL (US)

(72) Inventors: Patrick H. Benz, Sarasota, FL (US); Adam Reboul, Sarasota, FL (US)

(73) Assignee: BENZ RESEARCH AND DEVELOPMENT CORP., Sarasota, FL (US)

( * ) Notice: Subject to any disclaimer, the term of this patent is extended or adjusted under 35 U.S.C. 154(b) by 356 days.

(21) Appl. No.: 15/586,890

(22) Filed: May 4, 2017

(65) Prior Publication Data

US 2018/0169296 A1 Jun. 21, 2018

Related U.S. Application Data

(60) Provisional application No. 62/435,441, filed on Dec. 16, 2016.

(51) Int. Cl.
| | | |
|---|---|---|
| *A61L 27/16* | (2006.01) | |
| *A61F 2/16* | (2006.01) | |
| *G02B 1/04* | (2006.01) | |
| *C08L 33/04* | (2006.01) | |
| *C08F 220/28* | (2006.01) | |
| *A61L 27/50* | (2006.01) | |
| *C08F 220/30* | (2006.01) | |
| *C08F 220/32* | (2006.01) | |
| *C08F 220/56* | (2006.01) | |
| *C08F 220/58* | (2006.01) | |

(52) U.S. Cl.
CPC ............ *A61L 27/16* (2013.01); *A61F 2/16* (2013.01); *A61L 27/50* (2013.01); *C08F 220/28* (2013.01); *C08F 220/30* (2013.01); *C08F 220/32* (2013.01); *C08F 220/56* (2013.01); *C08F 220/58* (2013.01); *C08L 33/04* (2013.01); *G02B 1/041* (2013.01); *A61L 2430/16* (2013.01); *C08F 220/302* (2020.02); *C08F 220/325* (2020.02)

(58) Field of Classification Search
CPC ............ A61L 2430/16; G02B 1/041; C08F 2220/325; C08F 2220/281; C08F 2220/301; C08F 220/20; C08F 220/56; C08F 220/28; C08F 220/30; C08F 220/32; C08F 220/58; C08F 2220/302; C08L 33/06
See application file for complete search history.

(56) References Cited

U.S. PATENT DOCUMENTS

| | | | |
|---|---|---|---|
| 5,326,506 A | | 7/1994 | Vanderbilt |
| 5,532,289 A | * | 7/1996 | Benz .................. C08F 220/28 264/2.6 |
| 5,693,095 A | | 12/1997 | Freeman et al. |
| 6,267,784 B1 | | 7/2001 | Benz et al. |
| 6,365,652 B2 | | 4/2002 | Gupta et al. |
| 6,517,750 B2 | | 2/2003 | Benz et al. |
| 7,067,602 B2 | | 6/2006 | Benz et al. |
| 7,387,642 B2 | | 6/2008 | Benz et al. |
| 7,947,796 B2 | | 5/2011 | Benz et al. |
| 9,561,302 B2 | | 2/2017 | Benz et al. |
| 2002/0027302 A1 | | 3/2002 | Benz et al. |
| 2002/0058723 A1 | | 5/2002 | Benz et al. |
| 2002/0058724 A1 | | 5/2002 | Benz et al. |
| 2004/0010082 A1 | * | 1/2004 | Ichihara .............. A61L 27/16 525/60 |
| 2005/0131183 A1 | | 6/2005 | Benz et al. |
| 2006/0199929 A1 | | 9/2006 | Benz et al. |
| 2006/0276606 A1 | | 12/2006 | Benz et al. |
| 2008/0221235 A1 | | 9/2008 | Benz et al. |
| 2013/0253159 A1 | * | 9/2013 | Benz .................... A61L 27/16 526/313 |

FOREIGN PATENT DOCUMENTS

| | | |
|---|---|---|
| KR | 2012-0125918 A | 11/2012 |
| WO | WO-96/40303 A1 | 12/1996 |
| WO | WO-00/79312 A1 | 12/2000 |
| WO | WO-01/18079 A1 | 3/2001 |
| WO | WO-2010/128266 A1 | 11/2010 |
| WO | WO-2015/161199 A | 10/2015 |

OTHER PUBLICATIONS

Higashihara, T. et al. "Recent Progress in High Refractive Index Polymers." Macromolecules, vol. 48, 2015, pp. 1915-1929.
International Search Report and Written Opinion dated Apr. 6, 2018 in PCT/US2017/066370 (13 pgs.).
Garcia, F. et al. "Reaction Kinetics and Gel Effect on the Polymerization of 2-Ethoxyethyl Methacrylate and 2(2-Ethoxyethoxy) Ethyl Methacrylate." Journal of Polymer Science: Part A: Polymer Chemistry, vol. 40, 2002, pp. 3987-4001.

* cited by examiner

Primary Examiner — Alicia J Sawdon
(74) Attorney, Agent, or Firm — Foley & Lardner LLP

(57) ABSTRACT

A hydrophilic intraocular lens (IOL) with high refractive index comprising at least one copolymer comprising: ((a) a first monomeric subunit comprising (i) a polymerized (meth)acrylate group and an aliphatic carbon moiety comprising at least two hydroxyl substituents or (ii) a polymerized (meth)acrylamide group, (b) a second monomeric subunit different from the first monomeric subunit comprising a polymerized (meth)acrylate group, at least one side group comprising (i) an aryloxy moiety comprising at least one halogen, and (ii) an aliphatic carbon moiety linking the aryloxy moiety with the polymerized (meth)acrylate group, wherein the aliphatic carbon moiety comprises optionally at least one hydroxyl substituent, (c) a third monomeric subunit different from the first and second monomeric subunits comprising a polymerized (meth)acrylate group and at least one alkoxyalkoxyalkyl side group.

25 Claims, No Drawings

HIGH REFRACTIVE INDEX HYDROPHILIC MATERIALS

RELATED APPLICATIONS

This application claims priority to U.S. provisional application Ser. No. 62/435,441 filed Dec. 16, 2016, the complete disclosure of which is hereby incorporated by reference in its entirety.

BACKGROUND

Various types of intraocular lenses (IOLs) are known. For example, there are known one-piece intraocular lenses and composite intraocular lens having multiple pieces. A one-piece intraocular lens is one where both optic and non-optic portions are made from one material. The non-optic portions of IOLs are referred to as haptic portions, and are used for attachment purposes.

Both hydrophobic and hydrophilic foldable IOLs are described in the prior art in, for example, U.S. Pat. Nos. 7,947,796, 7,387,642, 7,067,602, 6,517,750 and 6,267,784 each of which is hereby incorporated by reference in its entirety. See also, for example, U.S. Patent Publication Nos. 2013/0253159, 2008/0221235, 2006/0276606, 2006/0199929, 2005/0131183, 2002/0058724, 2002/0058723 and 2002/0027302, along with WO/2015/161199, each of which is hereby incorporated by reference in its entirety.

Additionally, lens materials comprising the monomer 2-hydroxy-3-phenoxypropyl acrylate are disclosed in the prior art in, for example, WO 2010/128266, WO 2001/018079, WO 2000/079312, WO 96/40303, and U.S. Pat. No. 5,693,095. The lens material 2-ethoxyethyl methacrylate is also known in the art as a compound with a low glass transition temperature. See, for example, Garcia, F., et al., *J. of Polymer Science: Part A: Polymer Chemistry*, Vol. 40, 3987-4001 (2002).

A need exists, however, for improved IOL materials including hydrophylic materials, which have higher refractive indices, can provide an absence of stickiness characteristics after injection of the IOL, and can provide for difficult-to-achieve combinations of properties, such as small-incision injectability while maintaining good mechanical properties facilitating better surgical outcomes.

SUMMARY

Embodiments described herein include, for example, copolymers, lenses, intraocular lenses, blanks for intraocular lenses, and methods for making and methods of using compositions and intraocular lenses.

Some embodiments provide, for example, a hydrophilic intraocular lens comprising at least one copolymer comprising: (a) a first monomeric subunit comprising (i) a polymerized (meth)acrylate group and an aliphatic carbon moiety comprising at least two hydroxyl substituent or (ii) a polymerized (meth)acrylamide group, (b) a second monomeric subunit different from the first monomeric subunit comprising a polymerized (meth)acrylate group, at least one side group comprising (i) an aryloxy moiety comprising at least one halogen, and (ii) an aliphatic carbon moiety linking the aryloxy moiety with the polymerized (meth)acrylate group, wherein the aliphatic carbon moiety optionally comprises at least one hydroxyl substituent, (c) a third monomeric subunit different from the first and second monomeric subunits comprising a polymerized (meth)acrylate group and at least one alkoxyalkoxyalkyl side group.

In some embodiments, the first monomeric subunit comprises a polymerized (meth)acrylate group and an aliphatic carbon moiety comprising at least two hydroxyl substituent. In some embodiments, the copolymer further comprises a fourth monomeric subunit different from the first, second and third monomeric subunits comprising a polymerized (meth)acrylate group and at least one alkoxyalkyl side group. In some embodiments, the copolymer further comprises monomeric subunits that are crosslinked subunits. In some embodiments, the aryloxy group of the second monomeric subunit comprises a phenoxy group. In some embodiments, the aliphatic carbon moiety of the second monomeric subunit is substituted with one hydroxyl group. In some embodiments, the halogen in the second monomeric subunit is a bromo moiety. In some embodiments, the aliphatic carbon moiety of the second monomeric subunit is a $C_3$ moiety. In some embodiments, the aliphatic carbon moiety of the second monomeric subunit is represented by —$CH_2$—CHOH—$CH_2$—. In some embodiments, the alkoxyalkoxyalkyl group of the third monomeric subunit is a $C_3$ to $C_{12}$ group. In some embodiments, the alkoxyalkoxyalkyl group of the third monomeric subunit comprises two oxygen atoms. In some embodiments, the alkoxyalkoxyalkyl group of the third monomeric subunit is 2-ethoxyethoxyethyl. In some embodiments, the aliphatic carbon moiety comprising at least two hydroxyl substituents of the first monomeric subunit consists of two hydroxyl substituents. In some embodiments, the aliphatic carbon moiety comprising at least two hydroxyl substituents of the first monomeric subunit comprises a $C_2$ to $C_6$ aliphatic carbon moiety. In some embodiments, the first monomeric subunit comprises 2,3-dihydroxypropyl methacrylate. In some embodiments, the alkoxyalkyl group of the fourth monomeric subunit is a $C_3$ to $C_{12}$ group. In some embodiments, the alkoxyalkyl group of the fourth monomeric subunit comprises a single oxygen atom. In some embodiments, the alkoxyalkyl group of the fourth monomeric subunit is 2-ethoxyethyl. In some embodiments, the third monomeric subunit comprises polymerized 2-ethoxyethoxyethyl methacrylate and the second monomeric subunit comprises polymerized bromo-2-hydroxy-3-phenoxypropyl methacrylate.

In some embodiments, the first monomeric subunit is about 30% to about 50%, by weight of the copolymer composition, the second monomeric subunit is about 20% to about 40%, by weight of the copolymer composition, and the third monomeric subunit is about 20% to about 40%, by weight of the copolymer composition.

In some embodiments, the copolymer further comprises one or more of UV absorbers, initiation agents and/or crosslinking agents. In some embodiments, the copolymer further comprises monomeric subunits that are crosslinked subunits of a trimethacrylate crosslinker. In some embodiments, the copolymer has an equilibrium water content of 20 wt. % or more at 35° C. in isotonic saline. In some embodiments, the lens has a central thickness of up to 1 mm and unfolds in less than or about 1 minute when placed in a saline solution at a temperature of 35° C. In some embodiments, the lens has a central thickness of up to 1 mm and unfolds in 5 to 20 seconds, preferably 5 to 10 seconds. In some embodiments, the refractive index at 546 nm and 20° C. is about 1.47 to about 1.50. In some embodiments, the lens is capable of being injected through a tube that has an inner diameter of approximately 1.6 mm. In some embodiments, the refractive index at 546 nm and 20° C. is greater than 1.47.

Some embodiments provide, for example, a composition comprising at least one copolymer comprising: (a) a first monomeric subunit comprising (i) a polymerized (meth) acrylate group and an aliphatic carbon moiety comprising at least two hydroxyl substituents or (ii) a polymerized (meth) acrylamide group, (b) a second monomeric subunit different from the first monomeric subunit comprising a polymerized (meth)acrylate group, at least one side group comprising (i) an aryloxy moiety comprising at least one halogen, and (ii) an aliphatic carbon moiety linking the aryloxy moiety with the polymerized (meth)acrylate group, wherein the aliphatic carbon moiety comprises at least one hydroxyl substituent, (c) a third monomeric subunit different from the first and second monomeric subunits comprising a polymerized (meth)acrylate group and at least one alkoxyalkoxyalkyl side group, and (d) optionally a fourth monomeric subunit different from the first, second and third monomeric subunits comprising a polymerized (meth)acrylate group and at least one alkoxyalkyl side group.

In some embodiments, the first monomeric subunit comprises a polymerized (meth)acrylate group and an aliphatic carbon moiety comprising at least two hydroxyl substituents. In some embodiments, the copolymer further comprises monomeric subunits that are crosslinked subunits. In some embodiments, the aryloxy group of the second monomeric subunit comprises a phenoxy group. In some embodiments, the aliphatic carbon moiety of the second monomeric subunit is substituted with one hydroxyl group. In some embodiments, the halogen in the second monomeric subunit is a bromo moiety. In some embodiments, the alkoxyalkoxyalkyl group of the third monomeric subunit is 2-ethoxyethoxyethyl. In some embodiments, the aliphatic carbon moiety comprising at least two hydroxyl substituents of the first monomeric subunit consists of two hydroxyl substituents. In some embodiments, the aliphatic carbon moiety comprising at least two hydroxyl substituents of the first monomeric subunit comprises a $C_2$ to $C_6$ aliphatic carbon moiety. In some embodiments, the first monomeric subunit comprises 2,3-dihydroxypropyl methacrylate. In some embodiments, the alkoxyalkyl group of the fourth monomeric subunit is 2-ethoxyethyl. In some embodiments, the third monomeric subunit comprises polymerized 2-ethoxyethoxyethyl methacrylate and the second monomeric subunit comprises polymerized bromo-2-hydroxy-3-phenoxypropyl methacrylate. In some embodiments, the first monomeric subunit is about 30% to about 50%, by weight of the copolymer composition, the second monomeric subunit is about 20% to about 40%, by weight of the copolymer composition, and the third monomeric subunit is about 20% to about 40%, by weight of the copolymer composition. In some embodiments, the copolymer further comprises one or more of UV absorbers, initiation agents and/or crosslinking agents. In some embodiments, the copolymer further comprises monomeric subunits that are crosslinked subunits of a trimethacrylate crosslinker. In some embodiments, the copolymer contains 2 wt. % or less of residual unreacted monomer prior to being subjected to a purification step. In some embodiments, the copolymer contains 1 wt. % or less of residual unreacted monomer prior to being subjected to a purification step. In some embodiments, the copolymer contains 1 wt. % or less of residual unreacted monomer and has not been subjected to a purification step. In some embodiments, the copolymer consists of the first, second and third monomeric subunits, and optionally, one or more of the fourth monomeric subunit, UV absorbers, initiation agents and/or crosslinking agents. In some embodiments, the first monomeric subunit comprising a polymerized (meth)acrylamide group.

Some embodiments provide, for example, a method for making a composition comprising at least one copolymer, the method comprising: preparing a co-monomer mixture comprising (a) a first monomer comprising (i) a (meth) acrylate group and an aliphatic carbon moiety comprising at least two hydroxyl substituents or (ii) a (meth)acrylamide group, (b) a second monomer different from the first monomer comprising a (meth)acrylate group, at least one side group comprising (i) an aryloxy moiety comprising at least one halogen, and (ii) an aliphatic carbon moiety linking the aryloxy moiety with the (meth)acrylate group, wherein the aliphatic carbon moiety comprises at least one hydroxyl substituent, (c) a third monomer different from the first and second monomer comprising a (meth)acrylate group and at least one alkoxyalkoxyalkyl side group, (d) optionally a fourth monomer different from the first, second and third monomers comprising a (meth)acrylate group and at least one alkoxyalkyl side group; and polymerizing the co-monomer mixture by adding a photo or thermal initiator, for example, CGI 819 (photo) and Vazo type initiators.

In some embodiments, the initiator is a photo initiator. In some embodiments, the copolymer contains 2 wt. % or less of residual unreacted monomer after the polymerization step. In some embodiments, the copolymer contains 1 wt. % or less of residual unreacted monomer after the polymerization step. In some embodiments, the co-monomer mixture does not comprise a solvent. In some embodiments, the first monomer comprises a (meth)acrylate group and an aliphatic carbon moiety comprising at least two hydroxyl substituents. In some embodiments, the co-monomer mixture further comprises monomers that is capable of crosslinking. In some embodiments, the aryloxy group of the second monomer comprises a phenoxy group. In some embodiments, the aliphatic carbon moiety of the second monomer subunit is substituted with one hydroxyl group. In some embodiments, the halogen in the second monomer is a bromo moiety. In some embodiments, the alkoxyalkoxyalkyl group of the third monomer is 2-ethoxyethoxyethyl. In some embodiments, the aliphatic carbon moiety comprising at least two hydroxyl substituents of the first monomer comprises two hydroxyl substituents. In some embodiments, the aliphatic carbon moiety comprising at least two hydroxyl substituents of the first monomer comprises a $C_2$ to $C_6$ aliphatic carbon moiety. In some embodiments, the first monomer comprises 2,3-dihydroxypropyl methacrylate. In some embodiments, the alkoxyalkyl group of the fourth monomer is 2-ethoxyethyl. In some embodiments, the first monomer comprises 2-ethoxyethoxyethyl methacrylate and the second monomer comprises bromo-2-hydroxy-3-phenoxypropyl methacrylate. In some embodiments, the first monomer is about 20% to about 40%, by weight of the co-monomer composition, and the second monomer is about 20% to about 40%, by weight of the co-monomer composition, the third monomer is about 30% to about 50%, by weight of the co-monomer composition. In some embodiments, the co-monomer composition further comprises one or more of UV absorbers, initiation agents and/or crosslinking agents. In some embodiments, the co-monomer composition further comprises monomers comprising trimethacrylate capable of crosslinking.

At least one advantage for at least one embodiment includes higher refractive properties for an IOL, particularly for a hydrophilic index IOL.

At least one additional advantage for at least one embodiment includes good unfolding properties for an IOL. For example, an IOL embodied herein may unfold in five to ten seconds.

At least one additional advantage for at least one embodiment includes an absence of stickiness characteristics after injection of the IOL (e.g., the haptic does not stick to the optic).

At least one additional advantage for at least one embodiment includes a refractive index of greater than 1.47, 1.48, 1.49 or 1.50.

Yet another advantage for at least one embodiment is a high diopter IOL able to pass through a very small orifice injector, such as a 1.6 mm injector, e.g., a Medicel Accuject™ 1.6 mm.

Yet another advantage for at least one embodiment is an IOL with an Abbe value of 45 or higher.

DETAILED DESCRIPTION

Introduction

All references cited herein are incorporated by reference in their entirety.

Intraocular lens are generally known in the art. See, for example, U.S. Pat. Nos. 7,947,796; 7,387,642; 7,067,602; 6,517,750; and 6,267,784.

As used herein, the term "(meth)acrylate" refers to acrylic, esters of acrylic or methacrylic acid, amides, and other suitable derivatives of acrylic or methacrylic acid, and mixtures thereof. Illustrative examples of suitable (meth)acrylic monomers include, without limitation, the following methacrylate esters: methyl methacrylate, ethyl methacrylate, n-propyl methacrylate, n-butyl methacrylate (BMA), isopropyl methacrylate, isobutyl methacrylate, n-amyl methacrylate, n-hexyl methacrylate, isoamyl methacrylate, 2-hydroxyethyl methacrylate, 2-hydroxypropyl methacrylate, N,N-dimethylaminoethyl methacrylate, N,N-diethylaminoethyl methacrylate, t-butylaminoethyl methacrylate, 2-sulfoethyl methacrylate, trifluoroethyl methacrylate, glycidyl methacrylate (GMA), benzyl methacrylate, allyl methacrylate, 2-n-butoxyethyl methacrylate, 2-chloroethyl methacrylate, sec-butyl-methacrylate, tert-butyl methacrylate, 2-ethylbutyl methacrylate, cinnamyl methacrylate, crotyl methacrylate, cyclohexyl methacrylate, cyclopentyl methacrylate, 2-ethoxyethyl methacrylate, furfuryl methacrylate, hexafluoroisopropyl methacrylate, methallyl methacrylate, 3-methoxybutyl methacrylate, 2-methoxybutyl methacrylate, 2-nitro-2-methylpropyl methacrylate, n-octylmethacrylate, 2-ethylhexyl methacrylate, 2-phenoxyethyl methacrylate, 2-phenylethyl methacrylate, phenyl methacrylate, propargyl methacrylate, tetrahydrofurfuryl methacrylate and tetrahydropyranyl methacrylate. Example of suitable acrylate esters include, without limitation, methyl acrylate, ethyl acrylate, n-propyl acrylate, isopropyl acrylate, n-butyl acrylate (BA), n-decyl acrylate, isobutyl acrylate, n-amyl acrylate, n-hexyl acrylate, isoamyl acrylate, 2-hydroxyethyl acrylate, 2-hydroxypropyl acrylate, N,N-dimethylaminoethyl acrylate, N,N-diethylaminoethyl acrylate, t-butylaminoethyl acrylate, 2-sulfoethyl acrylate, trifluoroethyl acrylate, glycidyl acrylate, benzyl acrylate, allyl acrylate, 2-n-butoxyethyl acrylate, 2-chloroethyl acrylate, sec-butylacrylate, tert-butyl acrylate, 2-ethylbutyl acrylate, cinnamyl acrylate, crotyl acrylate, cyclohexyl acrylate, cyclopentyl acrylate, 2-ethoxyethyl acrylate, furfuryl acrylate, hexafluoroisopropyl acrylate, methallyl acrylate, 3-methoxybutyl acrylate, 2-methoxybutyl acrylate, 2-nitro-2-methylpropyl acrylate, n-octylacrylate, 2-ethylhexyl acrylate, 2-phenoxyethyl acrylate, 2-phenylethyl acrylate, phenyl acrylate, propargyl acrylate, tetrahydrofurfuryl acrylate and tetrahydropyranyl acrylate.

One embodiment provides an hydrophilic intraocular lens comprising at least one copolymer comprising:

(a) a first monomeric subunit comprising (i) a polymerized (meth)acrylate group and an aliphatic carbon moiety comprising at least two hydroxyl substituents or (ii) a polymerized (meth)acrylamide group, (b) a second monomeric subunit different from the first monomeric subunit comprising a polymerized (meth)acrylate group, at least one side group comprising (i) an aryloxy moiety comprising at least one halogen, and (ii) an aliphatic carbon moiety linking the aryloxy moiety with the polymerized (meth)acrylate group, wherein the aliphatic carbon moiety comprises at least one hydroxyl substituent, (c) a third monomeric subunit different from the first and second monomeric subunits comprising a polymerized (meth)acrylate group and at least one alkoxyalkoxyalkyl side group.

First Monomeric Subunit

The first monomeric subunit is derived from a hydrophilic monomer. In some embodiments, it can be the monomer subunit present in the largest amount as measured by weight percent for the copolymer or in an equal amount to another of the first three monomer subunit as measured by weight percent for the copolymer. The first monomeric subunit comprises a polymerizable moiety, such as acrylate, methacrylate, acrylamide and/or methacrylamide.

In some embodiments, the first monomeric subunit also comprises at least one carbon moiety comprising at least two hydroxyl substituents, e.g. 2, 3, 4 hydroxyl substituents. The first monomeric subunit may include hydrophilic monomeric subunits that are suitable for foldable IOLs. In some embodiments, the at least one carbon moiety comprising at least two hydroxyl substituents is a C2-C5 alkyl moiety comprising or consisting of 2, 3, 4 hydroxyl substituents. Examples include but are not limited to dihydroxypropyl (e.g., 2,3-dihydroxypropyl), dihydroxybutyl (e.g., 2,3-dihydroxybutyl, 2,4-dihydroxybutyl, 3,4-dihydroxybutyl), and the like.

In other embodiments, the first monomeric subunit comprises a polymerized (meth)acrylamide group. Examples include but are not limited to N,N-dimethyl(meth)acrylamide, ethoxyethyl(meth)acrylamide, acrylamide, dihydroxypropyl acrylamide, hydroxy ethyl acrylamide, hydroxy methyl acrylamide. In other embodiments, the first monomeric subunit comprising a polymerized (meth)acrylamide group also includes a C1-C5 alkyl moiety. In some embodiments, the first monomeric subunit comprising a polymerized (meth)acrylamide group also includes a C1-C5 alkyl moiety and one or more hydroxyl substituents, e.g. 1, 2, 3, 4 hydroxyl substituent(s).

Second Monomeric Subunit

The second monomeric subunit can be the monomer subunit present in the second largest amount as measured by weight percent for the copolymer or in an equal amount to the first monomer subunit as measured by weight percent for the copolymer. This subunit comprises a polymerizable moiety, such as acrylate, methacrylate, acrylamide and/or methacrylamide. The subunit also comprises an aliphatic spacer comprising one or more hydroxyl moieties. Finally, the second monomeric subunit comprises an optionally substituted aryl or aryloxy moiety comprising at least one halogen, including, for example, F, Cl, Br, and/or I. In another embodiment, the second monomeric subunit comprising a polymerized acrylate or methacrylate group may instead comprise a polymerized acrylamide or methacrylamide group that is optionally substituted at the nitrogen by hydrogen or a $C_1$ to $C_5$ alkyl. In some embodiments, the second monomer subunit comprises a polymerized methacrylate group.

For example, aryloxyalkyl methacrylate monomeric subunits can be represented by the formula Ar—O—$R_1$-MA where Ar is an optionally substituted aryl compound such as, for example, an optionally substituted phenyl, $R_1$ is an aliphatic spacer such as a bivalent alkyl group and "MA" is methacrylate. Alternatively, aryloxyalkyl acrylate monomeric subunits can be represented by the formula Ar—O—$R_2$-A where Ar is an optionally substituted aryl compound such as, for example an optionally substituted phenyl, $R_2$ is an aliphatic spacer such as a bivalent alkyl group and "A" is acrylate. Likewise, aryloxyalkyl acrylamide monomeric subunits can be represented by the formula Ar—O—$R_3$-AA where Ar is an optionally substituted aryl compound such as, for example, an optionally substituted phenyl, $R_3$ is an aliphatic spacer such as a bivalent alkyl group and "AA" is acrylamide. In addition, aryloxyalkyl methacrylamide monomeric subunits can be represented by the formula Ar—O—$R_4$-MAA where Ar is an optionally substituted aryl compound such as, for example, an optionally substituted phenyl, $R_4$ is an aliphatic spacer such as a bivalent alkyl group and "MAA" is methacrylamide. The bivalent group $R_1$, $R_2$, $R_3$, and $R_4$ may be further substituted by at least one hydroxy group. The AA or MAA monomeric subunits can be optionally substituted at the nitrogen by hydrogen or a $C_1$ to $C_5$ alkyl. Examples of $C_1$ to $C_5$ alkyl include methyl, ethyl, propyl, butyl, pentyl, and isomers thereof.

Both hydroxy and halogen-substituted aryloxyalkyl methacrylates and hydroxy and halogen-substituted aryloxyalkyl acrylates are ester-containing monomer compounds as will be recognized by those skilled in the art. Likewise, those skilled in the art would recognize hydroxy and halogen-substituted aryloxyalky acrylamides and hydroxy and halogen-substituted aryloxyalky methacrylamides as amide-containing monomer compounds.

In some embodiments, $R_1$, $R_2$, $R_3$, and $R_4$ can be independently selected from hydroxy-substituted alkyl groups having 1 to 5 carbon atoms and in some embodiments 1, 2, 3, 4, or 5 carbon atoms, the alkyl group is substituted by one or more hydroxy groups. With respect to $R_1$, it will be understood that the hydroxy-substituted alkyl group is bonded to the O of the Ar—O group and is also bonded to the O atom of the MA group. Similarly, with respect to $R_2$, it will be understood that the hydroxy-substituted alkyl group is bonded to the O of the Ar—O group and is also bonded to the O atom of the A group. Similarly, with respect to $R_3$, it will be understood that the hydroxy-substituted alkyl group is bonded to the O of the Ar—O group and is also bonded to the N atom of the AA group. Similarly, with respect to $R_4$, it will be understood that the hydroxy-substituted alkyl group is bonded to the O of the Ar—O group and is also bonded to the N atom of the MAA group. The hydroxy group may be substituted to any carbon of the alkyl group. Hydroxy-substituted alkyl groups that may be used in accordance with the embodiments herein include straight chain alkyl groups, including but not limited to methyl, ethyl, propyl, butyl, and pentyl groups, wherein at least one C—H is substituted for C—OH. Alkyl groups may also include branched chain isomers of straight chain alkyl groups including, but not limited to, the following, which are provided by way of example only: —CH($CH_3$)$_2$, —CH($CH_3$)($CH_2CH_3$), —CH($CH_2CH_3$)$_2$, —C($CH_3$)$_3$, and the like, wherein at least one C—H is substituted for C—OH. In some embodiments, the hydroxy-substituted aryloxyalkyl methacrylate or hydroxy-substituted aryloxyalkyl acrylate is selected where $R_1$ and $R_2$ have 1, 2, 3, or 4 carbon atoms.

Specific embodiments of $R_1$, $R_2$, $R_3$, and $R_4$ are by way of non-limiting example and the like. The AA or MAA monomeric subunits may be optionally substituted at the nitrogen by hydrogen or a $C_1$ to $C_5$ alkyl.

Aryloxy groups will be recognized by those skilled in the art to include an aryl compound bonded to an oxygen atom. In some embodiments, the aryl group comprises optionally substituted phenyl or naphthyl. In some embodiments, the aryl group may comprise one or more heteroatoms, such as by way of non-limiting example nitrogen or sulfur. The aryl moiety may be optionally substituted by one or more alkyl groups including but not limited to methyl, ethyl, propyl, butyl, and pentyl groups. The alkyl groups may be branched chain isomers of straight chain alkyl groups. The aryl moiety may be optionally substituted by one or more alkoxy groups comprising an alkyl group bound to an oxygen, the alkyl group comprising, but not limited to methyl, ethyl, propyl, butyl, and/or pentyl groups. The alkyl groups may be branched chain isomers of straight chain alkyl groups. Additionally the aryl moiety is substituted by one or more halogen groups, for example, F, Cl, Br, and/or I. In some embodiments, the aryl moiety is substituted by one halogen. In some embodiments, the aryl moiety is substituted by two, three, four, or five halogens. In some embodiments, wherein the aryl moiety is substituted by at least two halogens, the halogens can be the same or different.

Examples of some specific hydroxy and halogen-substituted aryloxyalkyl methacrylate, hydroxy and halogen-substituted aryloxyalkyl acrylate, hydroxy and halogen-substituted aryloxyalkyl methacrylamide and hydroxy and halogen-substituted aryloxyalkyl acrylamide monomeric subunits useful for forming the copolymers, but are not limited to, 2-bromo-2-hydroxy-3-phenoxypropyl acrylate, 3-bromo-2-hydroxy-3-phenoxypropyl acrylate, 4-bromo-2-hydroxy-3-phenoxypropyl acrylate, 2-bromo-2-hydroxy-3-phenoxypropyl methacrylate, 3-bromo-2-hydroxy-3-phenoxypropyl methacrylate, 4-bromo-2-hydroxy-3-phenoxypropyl methacrylate, 2-bromo-2-hydroxy-3-phenoxypropyl acrylamide, 3-bromo-2-hydroxy-3-phenoxypropyl acrylamide, 4-bromo-2-hydroxy-3-phenoxypropyl acrylamide, and/or 2-bromo-2-hydroxy-3-phenoxypropyl methacrylamide, 3-bromo-2-hydroxy-3-phenoxypropyl methacrylamide, or 4-bromo-2-hydroxy-3-phenoxypropyl methacrylamide. In some embodiments, the second monomer comprises bromo-2-hydroxy-3-phenoxypropyl methacrylate (BrHPPMA).

In some embodiments, the present copolymers may also include a second monomer that is represented by the general formula (II), wherein R' is hydrogen or methyl, Y is O or —NR", X is H, Cl, Br, —$CH_3$, or —$OCH_3$, n is 1 to 6, m is 1 to 6, R" is hydrogen or a $C_1$ to $C_5$ alkyl; and Z is H, OH or a halogen group.

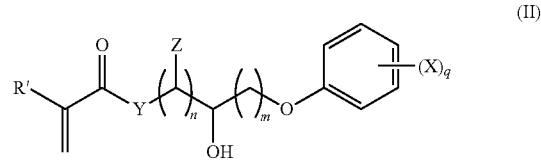

(II)

In other embodiments, n and m are 1 or 2 and X is Br, Z is H, and Y is O, and q is 1, 2, 3, 4, or 5. In some embodiments, q is 1 or 2.

Hence, one preferred embodiment provides an intraocular lens, wherein the second monomer subunit comprises a polymerized (meth)acrylate group. In another embodiment, the aryloxy group comprises a phenoxy group. In yet another embodiment, the aryloxy group comprises an unsubstituted phenoxy group. In another embodiment, the aliphatic carbon moiety of the second monomer is substituted with one hydroxyl group. In another embodiment, the aliphatic carbon moiety of the second monomer is a $C_3$ moiety. In another embodiment, the aliphatic carbon moiety of the second monomer is represented by —CH(Br)—CHOH—$CH_2$—. Finally, the side group of the second monomer, in one embodiment, comprises —CH(Br)—CHOH—$CH_2$—OPh, wherein OPh is an unsubstituted phenoxy group.

Third Monomeric Subunit

The third monomeric subunit comprises a polymerizable moiety, such as acrylate, methacrylate, acrylamide and/or methacrylamide. The subunit also comprises an alkoxyalkoxyalkyl side group. The third monomeric subunit may include monomeric subunits that are suitable for foldable IOLs. Examples include but are not limited to alkoxyalkoxyalkyl (meth)acrylates or alkoxyalkoxy (meth)acrylamides.

In another embodiment, the third monomeric subunit comprising a polymerized acrylate or methacrylate group may instead comprise a polymerized acrylamide or methacrylamide group that is optionally substituted at the nitrogen by hydrogen or a $C_1$ to $C_5$ alkyl. In some embodiments, the third monomer subunit comprises a polymerized methacrylate group.

Alkoxyalkoxyalkyl methacrylate monomeric subunits can be represented by the formula $R_{15}$—O—$R_5$—O—$R_6$-MA where $R_5$, $R_6$, $R_{15}$ are alkyl groups and "MA" is methacrylate. Alkoxyalkoxyalkyl acrylate monomeric subunits can be represented by the formula $R_{20}$—O—$R_7$—O—$R_8$-A where $R_7$, $R_8$, $R_{20}$ are alkyl groups and "A" is acrylate. Both alkoxyalkoxyalkyl methacrylates and alkoxyalkoxyalkyl acrylates are ester-containing monomer compounds as will be recognized by those skilled in the art. In some embodiments, $R_5$ to $R_8$, $R_{15}$, and $R_{20}$ can be independently selected from alkyl groups having 1 to 5 carbon atoms and in some embodiments 1, 2, 3, 4, or 5 carbon atoms. With respect to $R_6$, it will be understood that the alkyl group is bonded to the O of the $R_5$—O group and is also bonded to the O atom of the MA group. Similarly, with respect to $R_8$, it will be understood that the alkyl group is bonded to the O of the $R_7$—O group and is also bonded to the O atom of the A group. Alkyl groups that may be used in accordance with the embodiments herein include straight chain alkyl groups, including but not limited to methyl, ethyl, propyl, butyl, and pentyl groups. Alkyl groups may also include branched chain isomers of straight chain alkyl groups including, but not limited to, the following, which are provided by way of example only: —$CH(CH_3)_2$, —$CH(CH_3)(CH_2CH_3)$, —$CH(CH_2CH_3)_2$, —$C(CH_3)_3$, and the like. In some embodiments, the alkoxyalkoxyalkyl methacrylate or alkoxyalkoxyalkyl acrylate is selected where $R_5$, to $R_9$, $R_{15}$, and $R_{20}$ have 1, 2, 3, or 4 carbon atoms. Examples of some specific alkoxyalkoxyalkyl methacrylate and alkoxyalkoxyalkyl acrylate monomeric subunits useful for forming the copolymers of the embodiments herein include, but are not limited to, methoxymethoxyethyl methacrylate, ethoxyethoxyethyl methacrylate, propoxypropoxyethyl methacrylate, butoxybutoxymethyl methacrylate, methoxymethoxypropyl methacrylate, ethoxyethoxypropyl methacrylate, propoxypropoxypropyl methacrylate, butoxybutoxypropyl methacrylate, methoxymethoxybutyl methacrylate, ethoxyethoxybutyl methacrylate, propoxypropoxybutyl methacrylate, butoxybutoxybutyl methacrylate, methoxymethoxyethyl acrylate, ethoxyethoxyethyl acrylate, propoxypropoxyethyl acrylate, butoxybutoxymethyl acrylate, methoxymethoxypropyl acrylate, ethoxyethoxypropyl acrylate, propoxypropoxypropyl acrylate, butoxybutoxypropyl acrylate, methoxymethoxybutyl acrylate, ethoxyethoxybutyl acrylate, propoxypropoxybutyl acrylate, and butoxybutoxybutyl acrylate. In some preferred embodiments, the copolymer includes ethoxyethoxyethyl methacrylate (EOEOEMA).

Hence, a particularly preferred embodiment provides an intraocular lens, wherein the alkoxyalkoxyalkyl group is a $C_3$ to $C_{12}$ group. In one embodiment, the alkoxyalkoxyalkyl group comprises two oxygen atoms. In a specific embodiment, the alkoxyalkoxyalkyl group is 2-ethoxy ethoxy ethyl.

Optional Fourth Monomeric Subunit

In some embodiments, the copolymer can include a fourth monomeric subunit different from the first, second and third monomeric subunits comprising a polymerized (meth)acrylate group and one alkoxyalkyl side group.

Examples of such monomeric subunits used to make the fourth monomeric subunits include alkoxyalkyl methacrylate and/or alkoxyalkyl acrylate monomeric subunits. In some embodiments, the fourth monomeric subunit comprises a polymerized (meth)acrylate group and containing one alkoxyalkyl side group. Alkoxyalkyl methacrylate monomeric subunits can be represented by the formula $R_5$—O—$R_6$-MA where $R_5$ and $R_6$ are alkyl groups and "MA" is methacrylate. Alkoxyalkyl acrylate monomeric subunits can be represented by the formula $R_7$—O—$R_8$-A where $R_7$ and $R_8$ are alkyl groups and "A" is acrylate. Both alkoxyalkyl methacrylates and alkoxyalkyl acrylates are ester-containing monomer compounds as will be recognized by those skilled in the art. In some embodiments, $R_5$ to $R_8$ can be independently selected from alkyl groups having 1 to 5 carbon atoms and in some embodiments 1, 2, 3, 4, or 5 carbon atoms. With respect to $R_6$, it will be understood that the alkyl group is bonded to the O of the $R_5$—O group and is also bonded to the O atom of the MA group. Similarly, with respect to $R_8$, it will be understood that the alkyl group is bonded to the O of the $R_7$—O group and is also bonded to the O atom of the A group. Alkyl groups that may be used in accordance with the embodiments herein include straight chain alkyl groups, including but not limited to methyl, ethyl, propyl, butyl, and pentyl groups. Alkyl groups may also include branched chain isomers of straight chain alkyl groups including, but not limited to, the following, which are provided by way of example only: —$CH(CH_3)_2$, —$CH(CH_3)(CH_2CH_3)$, —$CH(CH_2CH_3)_2$, —$C(CH_3)_3$, and the like. In some embodiments, the alkoxyalkyl methacrylate or alkoxyalkyl acrylate is selected where $R_5$, to $R_8$ have 1, 2, 3, or 4 carbon atoms. Examples of some specific alkoxyalkyl methacrylate and alkoxyalkyl acrylate monomeric subunits useful for forming the copolymers of the embodiments herein include, but are not limited to, methoxyethyl methacrylate, ethoxyethyl methacrylate, propoxyethyl methacrylate, butoxymethyl methacrylate, methoxypropyl methacrylate, ethoxypropyl methacrylate, propoxypropyl methacrylate, butoxypropyl methacrylate, methoxybutyl methacrylate, ethoxybutyl methacrylate, propoxybutyl methacrylate, butoxybutyl methacrylate, methoxyethyl acrylate, ethoxyethyl acrylate, propoxyethyl acrylate, butoxymethyl acrylate, methoxypropyl acrylate, ethoxypropyl acrylate, propoxypropyl acrylate, butoxypropyl acrylate, methoxybutyl acrylate, ethoxybutyl acrylate, propoxybutyl acrylate, and butoxybutyl acrylate. In some preferred embodiments, the copolymer includes ethoxyethyl methacrylate (EOEMA).

Hence, a particularly preferred embodiment provides an intraocular lens, wherein the alkoxyalkyl group is a $C_3$ to $C_{12}$ group. In one embodiment, the alkoxyalkyl group comprises a single oxygen atom. In some embodiments, the alkoxyalkyl group is not a repeating alkoxyalkyl group. In a specific embodiment, the alkoxyalkyl group is 2-ethoxyethyl.

In some embodiments, an alkoxyalkyl methacrylate and/or alkoxyalkyl acrylate monomeric subunits are utilized in the copolymer disclosed herein to produce copolymers with a higher glass transition temperature.

In some embodiments, the co-polymers provided herein do not include the fourth monomeric subunit.

Optional Fifth Monomeric Subunit

In some embodiments, the copolymer can include a fifth monomeric subunit different from the first, second, third and fourth monomeric subunits comprising a polymerizable moiety, such as acrylate, methacrylate, acrylamide and/or methacrylamide. The subunit also comprises an aliphatic spacer comprising one or more hydroxyl moieties. Finally, the fifth monomeric subunit comprises an optionally substituted aryl or aryloxy moiety. In another embodiment, the fifth monomeric subunit comprising a polymerized acrylate or methacrylate group may instead comprise a polymerized acrylamide or methacrylamide group that is optionally substituted at the nitrogen by hydrogen or a $C_1$ to $C_5$ alkyl. In some embodiments, the fifth monomer subunit comprises a polymerized methacrylate group.

For example, aryloxyalkyl methacrylate monomeric subunits can be represented by the formula Ar—O—$R_1$-MA where Ar is an optionally substituted aryl compound such as, for example, an optionally substituted phenyl, $R_1$ is an aliphatic spacer such as a bivalent alkyl group and "MA" is methacrylate. Alternatively, aryloxyalkyl acrylate monomeric subunits can be represented by the formula Ar—O—$R_2$-A where Ar is an optionally substituted aryl compound such as, for example an optionally substituted phenyl, $R_2$ is an aliphatic spacer such as a bivalent alkyl group and "A" is acrylate. Likewise, aryloxyalkyl acrylamide monomeric subunits can be represented by the formula Ar—O—$R_3$-AA where Ar is an optionally substituted aryl compound such as, for example, an optionally substituted phenyl, $R_3$ is an aliphatic spacer such as a bivalent alkyl group and "AA" is acrylamide. In addition, aryloxyalkyl methacrylamide monomeric subunits can be represented by the formula Ar—O—$R_4$-MAA where Ar is an optionally substituted aryl compound such as, for example, an optionally substituted phenyl, $R_4$ is an aliphatic spacer such as a bivalent alkyl group and "MAA" is methacrylamide. The bivalent group $R_1$, $R_2$, $R_3$, and $R_4$ may be further substituted by at least one hydroxy group. The AA or MAA monomeric subunits can be optionally substituted at the nitrogen by hydrogen or a $C_1$ to $C_5$ alkyl. Examples of C1 to C5 alkyl include methyl, ethyl, propyl, butyl, pentyl, and isomers thereof.

Both hydroxy-substituted aryloxyalkyl methacrylates and hydroxy-substituted aryloxyalkyl acrylates are ester-containing monomer compounds as will be recognized by those skilled in the art. Likewise, those skilled in the art would recognize hydroxy-substituted aryloxyalky acrylamides and hydroxy-substituted aryloxyalky methacrylamides as amide-containing monomer compounds. In some embodiments, $R_1$, $R_2$, $R_3$, and $R_4$ can be independently selected from hydroxy-substituted alkyl groups having 1 to 5 carbon atoms and in some embodiments 1, 2, 3, 4, or 5 carbon atoms, the alkyl group is substituted by one or more hydroxy groups. With respect to $R_1$, it will be understood that the hydroxy-substituted alkyl group is bonded to the O of the Ar—O group and is also bonded to the O atom of the MA group. Similarly, with respect to $R_2$, it will be understood that the hydroxy-substituted alkyl group is bonded to the O of the Ar—O group and is also bonded to the O atom of the A group. Similarly, with respect to $R_3$, it will be understood that the hydroxy-substituted alkyl group is bonded to the O of the Ar—O group and is also bonded to the N atom of the AA group. Similarly, with respect to $R_4$, it will be understood that the hydroxy-substituted alkyl group is bonded to the O of the Ar—O group and is also bonded to the N atom of the MAA group. The hydroxy group may be substituted to any carbon of the alkyl group. Hydroxy-substituted alkyl groups that may be used in accordance with the embodiments herein include straight chain alkyl groups, including but not limited to methyl, ethyl, propyl, butyl, and pentyl groups, wherein at least one C—H is substituted for C—OH. Alkyl groups may also include branched chain isomers of straight chain alkyl groups including, but not limited to, the following, which are provided by way of example only: —CH(CH$_3$)$_2$, —CH(CH$_3$)(CH$_2$CH$_3$), —CH(CH$_2$CH$_3$)$_2$, —C(CH$_3$)$_3$, and the like, wherein at least one C—H is substituted for C—OH. In some embodiments, the hydroxy-substituted aryloxyalkyl methacrylate or hydroxy-substituted aryloxyalkyl acrylate is selected where $R_1$ and $R_2$ have 1, 2, 3, or 4 carbon atoms. Specific embodiments of $R_1$, $R_2$, $R_3$, and $R_4$ are by way of non-limiting example 1-hydroxy propyl, 2-hydroxy propyl, 3-hydroxy propyl, 2-hydroxy butyl, 3-hydroxy butyl, 2,3-dihydroxy butyl and the like. The AA or MAA monomeric subunits may be optionally substituted at the nitrogen by hydrogen or a $C_1$ to $C_5$ alkyl.

Aryloxy groups will be recognized by those skilled in the art to include an aryl compound bonded to an oxygen atom. In some embodiments, the aryl group comprises optionally substituted phenyl or naphthyl. In some embodiments, the aryl group may comprise one or more heteroatoms, such as by way of non-limiting example nitrogen or sulfur. The aryl moiety may be optionally substituted by one or more alkyl groups including but not limited to methyl, ethyl, propyl, butyl, and pentyl groups. The alkyl groups may be branched chain isomers of straight chain alkyl groups. The aryl moiety may be optionally substituted by one or more alkoxy groups comprising an alkyl group bound to an oxygen, the alkyl group comprising, but not limited to methyl, ethyl, propyl, butyl, and/or pentyl groups. The alkyl groups may be branched chain isomers of straight chain alkyl groups.

Examples of some specific hydroxy-substituted aryloxyalkyl methacrylate, hydroxy-substituted aryloxyalkyl acrylate, hydroxy-substituted aryloxyalkyl methacrylamide and hydroxy-substituted aryloxyalkyl acrylamide monomeric subunits useful for forming the copolymers, but are not limited to, 2-hydroxy-3-phenoxypropyl acrylate, 2-hydroxy-3-phenoxypropyl methacrylate, 2-hydroxy-3-phenoxypropyl acrylamide, and/or 2-hydroxy-3-phenoxypropyl methacrylamide. In some embodiments, the first monomer comprises 2-hydroxy-3-phenoxypropyl methacrylate (HPPMA).

In some embodiments, the present copolymers may also include a fifth monomer that is represented by the general formula (I), wherein R' is hydrogen or methyl, Y is O or —NR", X is H, —CH$_3$, or —OCH$_3$, n is 1 to 6, R" is hydrogen or a $C_1$ to $C_5$ alkyl.

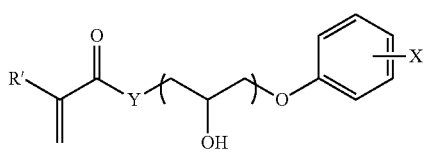 (I)

In other embodiments, n is 1 or 2 and X is hydrogen and Y is O.

Hence, one preferred embodiment provides an intraocular lens, wherein the fifth monomer subunit comprises a polymerized (meth)acrylate group. In another embodiment, the aryloxy group comprises a phenoxy group. In yet another embodiment, the aryloxy group comprises an unsubstituted phenoxy group. In another embodiment, the aliphatic carbon moiety of the fifth monomeric subunit is substituted with one hydroxyl group. In another embodiment, the aliphatic carbon moiety of the fifth monomeric subunit is a $C_3$ moiety. In another embodiment, the aliphatic carbon moiety of the fifth monomeric subunit is represented by —$CH_2$—CHOH—$CH_2$—. Finally, the side group of the fifth monomeric subunit, in one embodiment, comprises —$CH_2$—CHOH—$CH_2$—OPh, wherein OPh is an unsubstituted phenoxy group.

In some embodiments, the co-polymers provided herein do not include the fifth monomeric subunit.

Crosslinker (sixth Monomer)

The intraocular lens can comprise a copolymer that further comprises a sixth monomeric subunit that is crosslinked. In particular, di- or tri-functional crosslinking agents can be used to form the crosslinked subunits. However, other di- or multi-functional crosslinking agents known in the art may also be employed instead, or in addition to the di- or tri-functional crosslinking agents.

The copolymers can be prepared using conventional polymerization techniques known to those in the field of polymer chemistry. Crosslinkers may be employed in the polymerization reaction. For example, any crosslinking or difunctional monomer, can be used in effective amounts to give the desired crosslinking density. For example, in a concentration range of 0 to about 10 percent, such as about 0.01 to about 4 percent, or in some embodiments from 0.5 to 3 percent by weight, based on the weight of the polymer. Examples of suitable crosslinking agents include di-olefinic functional component, ethylene glycol dimethacrylate (EGDMA), diethylene glycol dimethacrylate ("DEGDMA"), triethylene glycol dimethacrylate, and the like. Generally, crosslinkers help to enhance the resulting copolymer's dimensional stability.

In some embodiments, the compositions include one or more crosslinker with three or more polymerizable functionalities (a multi-functional crosslinking agent). An example of a multi-functional crosslinking agent includes, but is not limited to, trimethylol propane trimethacrylate (TMPTMA). The analogous acrylate crosslinking agents, for example, trimethylol propane triacrylate, may also be utilized in place of any of their methacrylate analogs or in combination with the methacrylate analogs. Some embodiments include two or more tri-functional crosslinking agents or a multi-functional crosslinking agent and a di-functional crosslinking agent known in the art or incorporated herein by reference, such as for example EGDMA or DEGDMA. Therefore, in some embodiments, the copolymer compositions include EGDMA, DEGDMA, and/or TMPTMA. In some such embodiments, the amount of EGDMA and/or TMPTMA ranges from about 0.5 to about 5 (e.g., about 2 to about 3 or about 2.5 to about 3) percent by weight based on the weight of the dry copolymer In one embodiment, the only crosslinker used is a trifunctional crosslinker such as a trifunctional methacrylate crosslinker.

Examples of specific copolymers useful in the present embodiments are discussed in the examples where all weights are shown in grams.

Compositions/Amounts

The copolymers described herein can include the first and second monomeric subunits e.g. the alkoxyalkoxyalkyl methacrylate, alkoxyalkoxyalkyl acrylate, hydroxy and halogen-substituted aryloxyalkyl methacrylate, and hydroxy and halogen-substituted aryloxyalkyl acrylate monomeric subunits as the major components and the third and fourth monomeric subunits as the minor components, measured by weight.

Weight Amounts

In some embodiments, the copolymers provided herein may include about 20 to 60 percent, e.g., about 30 percent to about 50 percent by weight of the first monomeric subunit based on the total weight of the copolymer. In some embodiments, the first monomeric subunit includes about 30-40 percent, about 40-50 percent, or about 50-60 percent by weight of the copolymer. In some embodiments, the first monomeric subunit includes about 35-40 percent, about 40-45 percent, or about 45-50 percent by weight of the copolymer. In some embodiments, the first monomeric subunit includes about 40 percent, about 41 percent, about 42 percent, about 43 percent, about 44 percent, about 45 percent, about 46 percent, about 47 percent, about 48 percent, about 49 percent, about 50 percent by weight of the copolymer.

In some embodiments, the first monomeric subunit may include a hydrophilic monomeric subunit. In some embodiments, the hydrophilic monomeric subunit includes GMA. In other embodiments, the first monomeric subunit may include may include one or two or more different monomeric subunits, such as Am, DMA, EOEAm, HEAm, and the like.

While the present claims are not limited by theory, the presence of the first monomeric subunit provides for a high water content, as elaborated elsewhere in this disclosure.

In some embodiments, the copolymers provided herein can include about 10 percent to about 40 percent by weight of the second monomeric subunit based on the total weight of the copolymer. In some embodiments, the second monomeric subunit includes about 15-35 percent by weight of the copolymer. In some embodiments, the second monomeric subunit includes about 15-20 percent, about 20-25 percent, about 25-30 percent, about 30-35 percent, or about 35-40 percent by weight of the copolymer. In some embodiments, the second monomeric subunit includes about 20 percent, about 21 percent, about 22 percent, about 23 percent, about 24 percent, about 25 percent, about 26 percent, about 27 percent, about 28 percent, about 29 percent, about 30 percent, about 31 percent, about 32 percent, about 33 percent, about 34 percent, about 35 percent, about 36 percent, about 37 percent, about 38 percent, about 39 percent, or about 40 percent by weight of the copolymer.

In some embodiments, the second monomeric subunit includes BrHPPMA.

In the present copolymers, the total quantity of the one or more of the first and second monomeric subunits can make up the majority of the copolymer, as measured by weight. For example, in some embodiments, the total quantity of the combined amounts of any alkoxyalkoxyalkyl methacrylate, alkoxyalkoxyalkyl acrylate, hydroxy and halogen-substituted aryloxyalkyl methacrylate, and hydroxy and halogen-substituted aryloxyalkyl acrylate monomeric subunits may be about 55 percent to about 95 percent by weight based on the total weight of the copolymer. In some embodiments, the first and second monomeric subunits may include about 55-60 percent, about 55-65 percent, about 55-70 percent, about 55-75 percent, or about 55-80 percent by weight of the copolymer. In some embodiments, the first and second monomeric subunits may include about 55-65 percent, or about 65-75 percent by weight of the copolymer. In some embodiments, the first and second monomeric subunits may include about 55 percent, about 56 percent, about 57 percent, about 58 percent, about 59 percent, about 60 percent, about 61 percent, about 62 percent, about 63 percent, about 64 percent, about 65 percent, about 66 percent, about 67 percent, about 68 percent, about 69 percent, about 70 percent, about 71 percent, about 72 percent, about 73 percent, about 74 percent, about 75 percent, about 76 percent, about 77 percent, about 78 percent, about 79 percent, or about 80 percent by weight of the copolymer.

In some embodiments, the copolymers provided herein can include about 20 percent to about 40 percent by weight of the third monomeric subunit based on the total weight of the copolymer. In some embodiments, the third monomeric subunit includes about 20 percent, about 21 percent, about 22 percent, about 23 percent, about 24 percent, about 25 percent, about 26 percent, about 27 percent, about 28 percent, about 29 percent, about 30 percent, about 31 percent, about 32 percent, about 33 percent, about 34 percent, about 35 percent, about 36 percent, about 37 percent, about 38 percent, about 39 percent, or about 40 percent by weight of the copolymer.

In the present copolymers, the total quantity of the one or more of the third monomeric subunit will make up a minority of the polymer, as measured by weight.

In some embodiments, the copolymers provided herein may include about 0 to 15 percent by weight of the fourth monomeric subunit based on the total weight of the copolymer. In some embodiments, the fourth monomeric subunit may include about 5 to 10 percent or about 7 to 10 percent by weight of the copolymer. In some embodiments, the fourth monomeric subunit may include about 5 percent, about 6 percent, about 7 percent, about 8 percent, about 9 percent, about 10 percent, about 11 percent, about 12 percent, about 13 percent, about 14 percent, or about 15 percent by weight of the copolymer. In some embodiments, the fourth monomeric subunit may include about 7.5 percent by weight of the copolymer.

In some embodiments, the copolymers provided herein may include about 0% by weight of the fourth monomeric subunit based on the total weight of the copolymer.

In some embodiments, the copolymers provided herein may include about 0-25 percent by weight of the fifth monomeric subunit based on the total weight of the copolymer. In some embodiments, the fifth monomeric subunit may include about 0-10 percent, about 0-15 percent, or about 0-20 percent by weight of the copolymer. In some embodiments, the fifth monomeric subunit may include about 0 percent, about 1 percent, about 2 percent, about 3 percent, about 4 percent, about 5 percent, about 6 percent, about 7 percent, about 8 percent, about 9 percent, about 10 percent, about 11 percent, about 12 percent, about 13 percent, about 14 percent, about 15 percent, about 16 percent, about 17 percent, about 18 percent, about 19 percent, about 20 percent, about 21 percent, about 22 percent, about 23 percent, about 24 percent, or about 25 percent by weight of the copolymer. In some embodiments, the fifth monomeric subunit may include about 20 percent by weight of the copolymer.

In some embodiments, the fifth monomeric subunit is EOEMA. In some embodiments, the copolymers provided herein may include about 0% by weight of the fifth monomeric subunit based on the total weight of the copolymer.

In the present copolymers, the total quantity of the one or more of the crosslinking monomeric subunit will make up a minority of the copolymer. For example, in some embodiments, the total quantity of the combined amounts of incorporated crosslinking monomeric subunit ranges from about 0.5 percent to 3.0 percent by weight based on the total weight of the copolymer. In some embodiments, the crosslinking monomeric subunit may include about 0.5-1.0 percent, about 0.5-1.5 percent, about 0.5-2.0 percent, or about 0.5-2.5 percent by weight of the copolymer. In some embodiments, the crosslinking monomeric subunit may include about 0.5 percent, about 0.6 percent, about 0.7 percent, about 0.8 percent, about 0.9 percent, about 1.0 percent, about 1.1 percent, about 1.2 percent, about 1.3 percent, about 1.4 percent, about 1.5 percent, about 1.6 percent, about 1.7 percent, about 1.8 percent, about 1.9 percent, about 2.0 percent, about 2.1 percent, about 2.2 percent, about 2.3 percent, about 2.4 percent, about 2.5 percent, about 2.6 percent, about 2.7 percent, about 2.8 percent, about 2.9 percent, or about 3.0 percent by weight of the copolymer. In some embodiments, the crosslinking monomeric subunit may include about 2.74 percent by weight of the copolymer.

In some embodiments, the crosslinking monomeric subunit includes TMPTMA.

When a polymer or copolymer is said to include or contain a monomeric subunit such as ethoxyethyl methacrylate, it will be understood that this means that the ethoxyethyl methacrylate monomeric subunit has been reacted and incorporated into the polymer. A monomeric subunit of the claimed compounds may also be in the form of an oligomer that can be polymerized into the embodied copolymeric compounds.

In some embodiments, the copolymers may include about 20% to about 40%, by weight of the copolymer composition, and the second monomeric subunit is about 20% to about 40%, by weight of the copolymer composition, the third monomeric subunit is about 30% to about 50%, and about >0% to about 5% of the crosslinker.

In some embodiments, the copolymer compositions of the present embodiments consist of or consist essentially of a copolymer formed from the first, second and third monomeric subunits, and one or more crosslinking agent, and optionally, one or more UV absorbing compound or monomer, violet and/or blue absorber, or an antioxidant.

In some embodiments, the copolymer is formed from monomeric subunits consisting of GMA, bromo-2-hydroxy-3-phenoxypropyl (meth)acrylate, and 2-ethoxyethoxyethyl (meth)acrylate, and TMPTMA, and optionally, one or more UV absorbing compound or monomer, violet and/or blue absorber, or an antioxidant.

In some embodiments, a copolymer comprises, consists essentially of, or consists of:

(a) an incorporated (meth)acrylate group and an aliphatic carbon moiety comprising at least two hydroxyl substituents in an amount of from about 30 to 50 percent;

(b) an incorporated hydroxy and halogen-substituted aryloxyalkyl (meth)acrylate such as bromo-2-hydroxy-3-phenoxypropyl methacrylate in an amount of from about 20 to 40 percent;

(c) an incorporated alkoxyalkoxyalkyl (meth)acrylate such as 2-ethoxyethoxyethyl methacrylate in an amount of from about 20 to 40 percent;

(d) an incorporated crosslinker in an amount of from about >0% to about 5%; and (e) optionally, one or more optional other ingredients such as water, one or more UV absorbing compound or monomer, violet and/or blue absorber, and an antioxidant.

In some embodiments, the first, second, and third monomeric subunits together comprise about 70, 75, 80, 85, and/or 90 percent or more of the monomeric subunits composition by weight.

Properties of Composition

The copolymers can have a water content of more than or about 15 percent, or more than about 20 percent, based on the weight of the copolymer after it is fully equilibrated in water. In some embodiments, the copolymers have a water content at equilibrium that ranges from at or about 15 percent to at or about 25 percent based on the weight of the copolymer after it is fully equilibrated in water. In other embodiments, the water content ranges from about 20 percent to about 30 percent by weight of the copolymer after it is fully equilibrated with water.

The copolymers can possess superior mechanical and optical properties over other materials used to make IOLs, for example an increased refractive index over the prior art, which also remain foldable, and high in Abbe value. The components of present embodiments can provide for a hydrophilic lens with reduced stickiness providing for an IOL with desirable and reliable unfolding times, while maintaining a high refractive index.

The copolymers can possess superior refractive index compared to known hydrophilic lenses, e.g., Benz IOL25 (See U.S. Pat. No. 6,517,750; copolymer of 2-Hydroxyethylmethacrylate and 2-ethoxyethylmethacrylate). In some embodiments, the refractive index of the copolymers of the disclosure is greater than about (or about) 1.47, 1.48, 1.49 or 1.50. These refractive indices may be measured on a hydrated or non-hydrated lens.

The copolymers can be designed to have a wide range of physical characteristics. In some embodiments, a copolymer of the present disclosure can be designed to have glass transition temperatures above at or about 35° C., for example about 35° C. to about 100° C. In preferred embodiments, the glass transition temperature will be more than or about 30° C., 35° C., 40° C., 45° C., 50° C., 55° C., 60° C., 65° C., 70° C., 75° C., 80° C., 85° C., 90° C., 85° C., 100° C. These higher glass transition temperatures may be obtained from a non-hydrated copolymer. For example, a copolymer that has not been placed, for example, in isotonic saline or water.

Because the present copolymers are hydrophilic, they can also have equilibrium water contents that are about 15 percent or more, for example 15 percent, 16 percent, 17 percent, 18 percent, 19 percent, 20 percent, 21 percent, 22 percent, 23 percent, 24 percent, 25 percent or more. Due to their high water contents, the present copolymers are generally considered as hydrophilic. Generally, the present lenses also have advantageous properties compared to prior lenses because they have a comparable or higher refractive index than lenses containing, e.g., Benz IOL25 (See U.S. Pat. No. 6,517,750; copolymer of 2-Hydroxyethylmethacrylate and 2-ethoxyethylmethacrylate) and are more flexible, e.g., foldable, than other hydrophilic lenses that include aromatic monomeric subunits to increase the refractive index of the resulting polymer.

In some embodiments, the present copolymers can have an Abbe value of greater 45, or 46. In some embodiments, the present copolymers can have an Abbe value of 45, 46, 47, 48, or 49. In some embodiments, the present copolymers can have an Abbe value of 47. The human lens has an Abbe value of about 47. A high Abbe value indicates low chromatic aberration, which is a desirable quality for IOLs. Accordingly, in certain embodiments, the IOLs of the present disclosure have an Abbe value of 45, 46, 47, 48, or 49.

In some embodiments, the Abbe value can be measured by the following formula:

$$\text{Abbe Value} = (\text{Refractive Index at 589 nm} - 1)(\text{Refractive Index at 486 nm} - \text{Refractive Index at 656 nm})$$

In some embodiments, the copolymer contains a low amount of resicual unreacted monomer after polymerization. In some embodiments, the polymerization is run neat (i.e., without a solvent). In some embodiments, the copolymer contains 2 wt. % or less, or 1 wt. % or less, or 0.5 wt. % or less of residual unreacted monomer without being subjected to a purification step.

Lens

A present embodiment also provides intraocular lenses made at least partially from the present copolymers. Such intraocular lenses include an optic portion and one or more haptic portions. Typically, the copolymers of the embodiments will make up part or the entire optic portion of the intraocular lens. In some embodiments, the optic portion of the lens will have a core made from one of the present copolymer surrounded by different polymer or material. Lenses in which the optic portion is made up of at least partially of one of the present copolymers will usually also have a haptic portion. The haptic portion can also be made of copolymer of the embodiments or can be made of a different material, for example another polymer.

In some embodiments, the present intraocular lens is a one-piece lens having a soft, foldable central optic region and an outer peripheral region (haptic-region) in which both regions are made of the same polymer. In other embodiments, the optic and haptic regions can be formed from different types of polymers or materials, if desired. Some lenses can also have haptic portions that are made up of different materials, for example where one or more haptic portions is made from the same material as the optic portion and other haptic portions are made of materials other than a polymer of the embodiments. Multicomponent lenses can be made by embedding one material in the other, concurrent extrusion processes, solidifying the hard material about the soft material, or forming an interpenetrating network of the rigid component into a preformed hydrophilic core. In instances where one or more haptic portions are made from a different material than the optic portion of the lens, the haptic portion can be attached to the optic portion in any manner known in the art, such as by drilling a hole or holes in the optic portion and inserting the haptic portion.

The copolymers of the present embodiments can be designed so that they are capable of being folded so that the intraocular lens can be inserted into the eye of an individual through a small incision. The haptic portion of the lens provides the required support for the lens in the eye after insertion and unfolding of the lens and tends to help stabilize the position of the lens after insertion and the closure of the incision. The shape of the haptic portion design is not particularly limited and can be any desired configuration, for example, either a plate type or graduated thickness spiral filaments, also known as a C-loop design.

The optic portion of an IOL can be approximately 6 mm in diameter prior to hydration. The 6 mm diameter is fairly standard in the art, and is generally chosen to cover the pupil in its fully dilated state under naturally occurring conditions. However, other sizes are possible and the present embodiments are not limited to any particular diameter or size of intraocular lens. Furthermore, it is not necessary that the lens optic portion be circular; it could also be oval, square, or any other shape as desired.

The intraocular lens can further include one or more non-optical haptic components of an IOL extending away from the outermost peripheral surface of the optic portion. The haptic components can be of any desired shape, for example, graduated spiral filaments or flat plate sections and are used to support the lens within the posterior chamber of the eye. Lenses having any desired design configuration can be fabricated. Should the intraocular lens include other components besides the optical and haptic portions, such other portions can be made of a polymer as are the haptic and optic portions, or if desired, another material.

The intraocular lenses of the embodiments may be inserted into the eye in known manners. For example, the intraocular lens may be folded prior to insertion into the eye by small, thin forceps of the type typically used by ophthalmic surgeons. After the lens is in the targeted location, it is released to unfold. As is well known in the art, typically the lens that is to be replaced is removed prior to insertion of the intraocular lens. The intraocular lens of the present embodiments can be made of a generally physiologically inert soft polymeric material that is capable of providing a clear, transparent, refractive lens body even after folding and unfolding. In some embodiments, the foldable intraocular lens of the present embodiments can be inserted into any eye by injection whereby the mechanically compliant material is folded and forced through a tube such as a 1 mm to 3 mm inner diameter tube. In one embodiment the tube has an inner diameter of approximately 2.0 or 1.9 or 1.8 or 1.7 or 1.6 or 1.5 mm or less. In one embodiment the inner diameter is approximately 1.4 to 2.0 mm. In one embodiment, the inner diameter is approximately 1.8 mm, in another it is 1.6 mm. In one embodiment, the finished IOL lens is microinjectable (e.g. able to be injected through a tube that has an inner diameter of approximately 1.6 mm), such as a 1.6 Medi-cell injector.

Methods of Making Composition

The copolymers of the embodiments herein can be prepared using conventional polymerization techniques known to those in the field of polymer chemistry. Crosslinkers, also referred to as crosslinking agents, may be employed in the polymerization reaction. For example, any suitable cross-linking di-functional, multi-functional monomer, or combination of these can be used in effective amounts to give the desired crosslinking density. For example, in a concentration range of 0.5 to about 5 (e.g., about 2 to about 3 or about 2.5 to about 3) percent by weight based on the weight of the dry copolymer. Examples of suitable crosslinking agents include di-olefinic compounds such as ethylene glycol dimethacrylate (EGDMA), DEGDMA, and tetraethylene glycol dimethacrylate (TEGDMA) and other cross-linking agents such as trimethylol propane trimethacrylate (TMPTMA) which include three or more olefinic polymerizable functionalities. Generally, crosslinkers help to enhance the resulting polymer's dimensional stability.

Also, if desired an initiator can be used in the polymerization. Any initiator commonly used in the art, such as azo derivatives, like 2,2-azobis (2,4-dimethylvaleronitrile) and propanenitrile,2-methyl,2,2'-azobis, can be used. The initiator may also be a photo initiator, a thermal initiator, or other type of initiator as recognized by one skilled in the art. In some embodiments, the photo initiator is CGI 819. The initiator is used in an amount effective for initiation purposes, and is generally present from about 0.01 to 1.0 percent by weight, based on the weight of the polymer.

The copolymers of the present embodiments can also include additional monomers, such as, but not limited to, monomers that impart ultraviolet (UV) absorption to the polymer and/or monomers that impart absorption to the lens, such as blue light-blocking. UV absorbing monomers are typically aromatic compounds with olefinic functionality. The advantageous UV absorbing compounds can be added prior to polymerization for incorporation into the resultant polymer, as is well known in the art. The UV absorber should preferably be capable of polymerization into the lens matrix so as to be stable under physiological conditions. Any monomer copolymerizable with the described monomeric subunits can optionally be used, so long as such monomer does not materially or adversely affect the basic characteristics of the intraocular lens. Examples of useful additional monomers that can be used are described in U.S. Pat. No. 5,326,506, hereby incorporated by reference, directed to a composite intraocular lens. Additionally, aryl-substituted triazole compounds, such as for example, tris-aryl triazole compounds described in U.S. Pat. No. 6,365,652 or in U.S. Ser. No. 13/619,043 (e.g., UVX) may be used in at low concentrations to achieve desired UV absorbing properties. Such optional additional monomers, preferably are present in a total amount of not more than 10 weight percent, generally less than 5 weight percent, based on the total weight of the polymer.

In some embodiments, the polymerization reaction is conducted without any solvent.

As described above, it may be useful to add crosslinking agents such as EGDMA, DEGMA, TEGDMA, or TMPTMA, for example, to enhance the resulting polymer's dimensional stability. It may also be advantageous to add UV absorbing compounds with the lens monomeric subunits prior to polymerization for incorporation into the resultant polymer. The UV absorber should preferably be capable of polymerization into the lens matrix so as to resist extraction under physiologic conditions. The UV-absorbing monomer can be present in an amount effective to give the desired UV-absorbing properties, generally less than 4 percent by weight of the polymer, such as from 0.01 to about 1 percent by weight of the polymer. UV absorbers include those known in the art, such as, Natural Yellow, benzotriazoles, those in U.S. Ser. No. 13/619,043 (e.g., UVX), and the like.

Examples of specific copolymers useful in the present embodiments are included in Table 1 which are also discussed in the examples where all weights used in the polymerization are shown in grams with the percentage of the monomeric subunits in the polymer shown in parenthesis based on the total of all monomeric subunits and crosslinking agents and assuming incorporation of all monomeric subunits and crosslinkers in the copolymers.

In some embodiments, the method does not include a purification step after formation of the polymer due to low residual unreacted monomer.

Formation of IOL

The intraocular lenses of the present embodiments may be formed by methods known in the art. For example, in an exemplary process, the monomeric subunits that form the copolymer can be polymerized into a polymer rod, polymer blanks or discs are formed from the rod, and then the blanks are cut, for example, by a lathing and milling into the intraocular lens. The rods can be made by a procedure which begins with polymerizing, in a mold, such as in a tubular or cylindrical mold, a mixture of initiator and monomeric subunits, to form an optically clear soft lens body. As discussed above, it may be desirable to incorporate cross-linking materials and ultraviolet-absorbing compounds during polymerization or into the resultant polymer matrix. In some embodiments, the polymer rods are then cut and ground or otherwise machined, into blanks of the desired diameter and thickness by lathe cutting and machine milled.

Generally, the composite material rod is lathe cut or ground to a diameter 0.5 to 2.0 mm thicker than the required distance from the center of the lens body to the furthest edge of the legs or haptics. This rod is then cut into blanks of uniform thickness. The blanks are ground and lapped to a diameter and thickness suitable for lathe cutting and machine milling in the conventional manner into the intraocular lens of the present embodiments.

A general description of a stepwise process for forming the blanks into intraocular lenses is set forth in the flow chart below. One having ordinary skill in the field of intraocular lens manufacturing, from a review of the present specification, can make intraocular lenses using the general knowledge in the art on intraocular lens manufacture and the process of cryogenic machining.

Intraocular lenses can also be made by molding the present copolymer to form all or part of the optic portion of the lens. For example, the present copolymer can be polymerized in a mold by a liquid mixture of monomeric subunits and additional components, to form an optically clear soft lens body. These molding methods can involve molding the optics on one half of the lens, such as the anterior or posterior portion, or fully molding the lens. When only half of the optic portion of the lens is formed in the mold then the second side optics can be machined, for example as discussed above. In either of these embodiments, additional material can be molded to allow machining of various haptic designs. The copolymer may be optionally molded in the form of a preformed lens as known in the art as a universal blank.

Applications

One application is lens, including lens adapted for the human eye, including IOLs.

Additional embodiments are provided in the following non-limiting working examples and contrasted with comparative examples.

WORKING EXAMPLES

GMA refers to glycerol methacrylate or 2,3-dihydroxypropyl methacrylate

Am refers to acrylamide

DMA refers to N,N-dimethylacrylamide

EOEAm refers to 2-ethoxyethyl acrylamide

HEAm refers to hydroxy ethyl acrylamide

HPPMA refers to 2-hydroxy-3-phenoxypropyl methacrylate

Br-HPPMA refers to 4-bromo-2-hydroxy-3-phenoxypropyl methacrylate

EOEOEA refers to ethoxyethoxyethyl acrylate

EOEOEMA refers to ethoxyethoxyethyl methacrylate

EOEMA refers to 2-ethoxyethyl methacrylate

TMPTMA refers to trimethylol propane trimethacrylate

Example 1

Preparation of 4-bromo-2-hydroxy-3-phenoxypropyl methacrylate

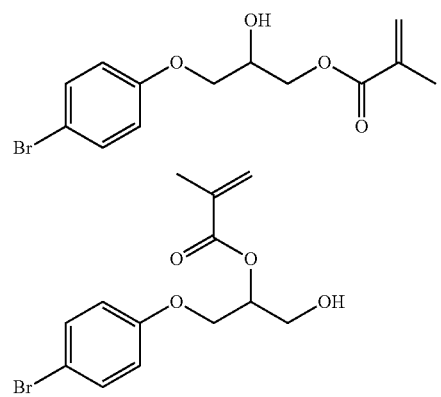

Scheme 1.

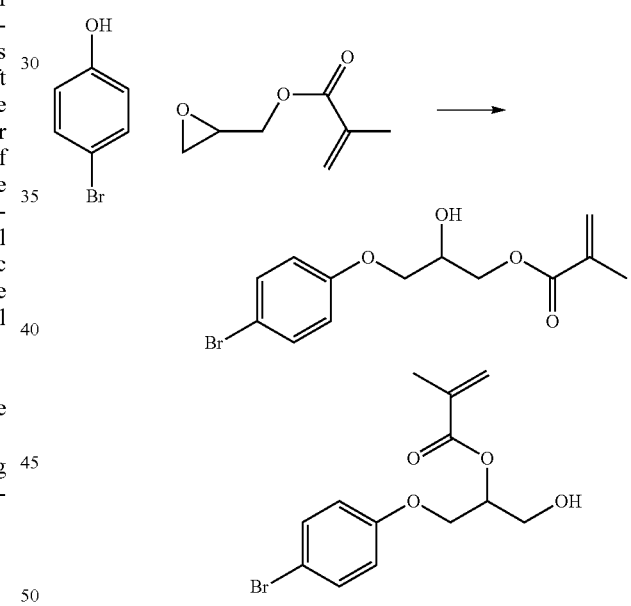

| Reactant/Solvent | Source | Mol Wt. | Mass (g) | Vol (L) | Mol | eq. |
|---|---|---|---|---|---|---|
| 4-bromoPhenol | Aldrich | 173.01 | 100 | | 0.58 | |
| Glycidyl methacrylate (GMA) | AK Sci | 142.15 | 107 | | 0.75 | 1.3 |
| Tetraethylammonium bromide (TEAB) | Aldrich | 210.36 | 24 | | 0.12 | 0.2 |
| DMF, anhydrous | Aldrich | | | 1 | | |

Under $N_2$, 4-bromophenol, anhydrous DMF was added into flask at room temp. TEAB, and GMA with anhydrous DMF (Total 1 L) was added. The mixture was slowly heated to 70° C. and kept at 70° C. for 2 days. Thin layer chromatography (TLC) showed no more staring material and only product. The reaction mixture was cooled to room temp. Water (2 L) was added. The extraction was carried out by using ethyl acetate (EtOAc) (2×1 L). The EtOAc layers were washed with 10% KOH aqueous and then water and then dried over anhydrous $Na_2SO_4$. The organic layers were filtered. The solvent was removed. The residue was purified by column chromatography on silica gel, eluting with hexanes (hex), and then 5% EtOAc/hex. 87 g of white solid was collected. The white solid was dissolved in $CH_2Cl_2$ (200 mL). The $CH_2Cl_2$ solution was washed with 10% KOH aqueous, and then water. Solvent was removed. The solid was dissolved in acetone (20 mL). Hexane (100 mL) was added until the solution turning cloudy (1 drop of acetone turned it to be clear). This solution was kept at room temp for overnight, and the white solid was precipitated. The solution was filtered and dried. The white solid was collected (45 g): mp: 68-69° C.; HPLC: 99.7%; GC: 100%.

Acid content test: Methanol/water (2:1, 200 mL) was neutralized with 0.02 N NaOH aqueous with phenolphthalein. 2 g of the product was added to be dissolved. The NaOH aqueous (0.02 N) was added and the red color was not disappeared within 1 minute.

Example 2

Preparation of 2-hydroxy-3-phenoxypropyl methacrylate

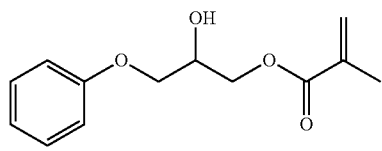

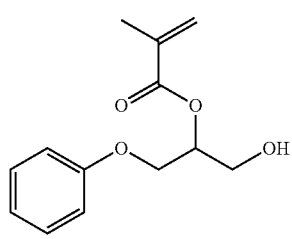

Scheme 2.

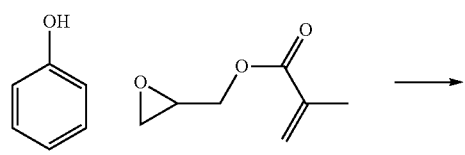

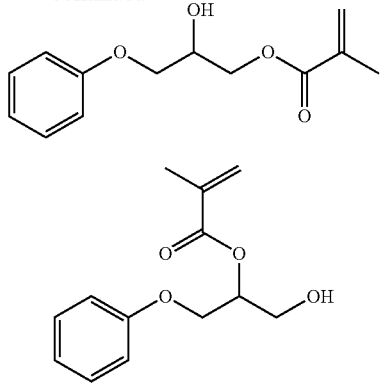

| Reactant /Solvent | Mass (g) | Vol (L) | Mol | eq. |
|---|---|---|---|---|
| Phenol | 188 | | 2.0 | |
| GMA | 370 | | 2.6 | 1.3 |
| Tetraethylammonium bromide (TEAB) | 84 | | 1.4 | 0.2 |
| DMF, anhydrous | | 1.5 | | |

Under $N_2$, phenol, anhydrous DMF was added into flask at room temp. TEAB, and GMA with anhydrous DMF (Total 1.5 L) was added. The mixture was slowly heated to 70° C. and kept at 70° C. for 2 days. TLC showed no more staring material and only product. The reaction mixture was cooled to room temp. Water (2 L) was added. The extraction was carried out by using EtOAc (3×1 L). The EtOAc layers were washed with 10% KOH aqueous and then water and dried over anhydrous $Na_2SO_4$. The organic layers were filtered. The solvent was removed. The residue was purified by column chromatography on silica gel, eluting with hex, and then 5% EtOAc/hex. 210 g of colorless oil was collected. The crude oil was dissolved in $CH_2Cl_2$ (300 mL). The $CH_2Cl_2$ solution was washed with 10% KOH aqueous, and then water. Solvent was removed. The oil was dissolved in acetone (50 mL). Hexane (300 mL) was added until the solution turning cloudy (1 drop of acetone turned it to be clear). This solution was kept in refrigerator for 2 days, and was shaken very often until the white solid was precipitated. The solution was filtered, dried. The white solid was collected (135 g): mp: 28-29° C.; HPLC: 99.6%; GC: 99.1%.

Acid content test: Methanol/water (2:1, 200 mL) was neutralized with 0.02 N NaOH aqueous with phenolphthalein. 2 g of the product was added to be dissolved. The NaOH aqueous (0.02 N) was added and the red color was not disappeared within 1 minute.

Polymer Examples

Unless otherwise noted, the following polymerizations were conducted on a 4-5 g scale.

Example 3

The monomers listed in the following table were combined and mixed. The homogenous mixture was degassed. The mixture was dispensed into molds and photo-cured at 0.25 mW/$cm^2$ for 60 min at 30° C. followed by 3.0 mW/$cm^2$ for 10 min at 85° C. The molds were allowed to cool to room temperature. The molds were opened and the polymer disc was removed and inspected. The polymer displayed properties summarized in Table 1.

TABLE 1

| Component | Wt % | MW (g/mol) | Mole % | Water Content (%) | RI$_{546nm}$ | Tg (Dry) |
|---|---|---|---|---|---|---|
| GMA | 50 | 160.17 | 59.6 | 32 | — | — |
| EOEOEMA | 30 | 202.25 | 28.3 | | | |
| Br-HPPMA | 20 | 315.16 | 12.1 | | | |
| GMA | 35 | 160.17 | 43.3 | 22 | 1.4705 | 39 |
| EOEOEMA | 45 | 202.25 | 44.1 | | | |
| Br-HPPMA | 20 | 315.16 | 12.6 | | | |
| GMA | 30 | 160.17 | 33.9 | 24 | 1.4694 | 60 |
| HEMA | 20 | 130.14 | 27.8 | | | |
| EOEOEMA | 30 | 202.25 | 26.8 | | | |
| Br-HPPMA | 20 | 315.16 | 11.5 | | | |
| GMA | 30 | 160.17 | 35.0 | 18.4 | 1.4885 (20 C) 1.4850 (35 C) | 67 |
| HEMA | 20 | 130.14 | 28.7 | | | |
| EOEOEMA | 20 | 202.25 | 18.5 | | | |
| Br-HPPMA | 30 | 315.16 | 17.8 | | | |
| GMA | 35 | 160.17 | 44.9 | 18.6 | 1.4850 (20 C) 1.4830 (35 C) | 43 |
| EOEOEMA | 35 | 202.25 | 35.6 | | | |
| Br-HPPMA | 30 | 315.16 | 19.6 | | | |
| GMA | 35 | 160.17 | 44.7 | 16.7 | 1.4945 (20 C) 1.4910 (35 C) | 51 |
| EOEOEMA | 30 | 202.25 | 30.4 | | | |
| Br-HPPMA | 25 | 315.16 | 16.2 | | | |
| HPPMA | 10 | 236.26 | 8.7 | | | |
| EOEAm | 35 | 143.18 | 47.7 | 12.3 | 1.4895 (20 C) 1.4845 (35 C) | 38 |
| EOEOEMA | 35 | 202.25 | 33.8 | | | |
| Br-HPPMA | 30 | 315.16 | 18.6 | | | |
| Am | 10 | 71.08 | 22.9 | 27.3 | 1.4693 (20 C) 1.4645 (35 C) | 60 |
| DMA | 10 | 99.13 | 16.4 | | | |
| EOEAm | 15 | 143.18 | 17.0 | | | |
| EOEOEMA | 35 | 202.25 | 28.2 | | | |
| Br-HPPMA | 30 | 315.16 | 15.5 | | | |
| DMA | 15 | 99.13 | 28.0 | 19.0 | — | 46 |
| EOEAm | 15 | 143.18 | 19.4 | | | |
| EOEOEMA | 35 | 202.25 | 32.0 | | | |
| Br-HPPMA | 35 | 315.16 | 20.6 | | | |
| Am | 5 | 71.08 | 12.3 | 21.6 | 1.4836 (20 C) 1.4812 (35 C) | 61 |
| DMA | 10 | 99.13 | 17.7 | | | |
| EOEAm | 20 | 143.18 | 24.5 | | | |
| EOEOEMA | 30 | 202.25 | 26.0 | | | |
| Br-HPPMA | 35 | 315.16 | 19.5 | | | |
| GMA | 40 | 160.17 | 49.9 | | 1.4817 (35 C) | 62 |
| EOEOEMA | 25 | 202.25 | 24.7 | | | |
| Br-HPPMA | 30 | 315.16 | 19.0 | | | |
| EOEMA | 5 | 158.19 | 6.3 | | | |
| GMA | 40 | 160.17 | 50.6 | 21.7-23.5 | 1.4815 (20 C) 1.4752-1.4815 (35 C) | 53-57 |
| EOEOEMA | 30 | 202.25 | 30.1 | | | |
| Br-HPPMA | 30 | 315.16 | 19.3 | | | |
| GMA | 38 | 160.17 | 48.7 | | — | — |
| EOEOEMA | 30 | 202.25 | 30.5 | | | |
| Br-HPPMA | 32 | 315.16 | 20.8 | | | |
| GMA | 38 | 160.17 | 48.5 | Solution Not Stable | 1.4850 (35 C) | 58 |
| EOEOEMA | 30 | 202.25 | 30.3 | | | |
| HPPMA | 2 | 236.26 | 1.7 | | | |
| Br-HPPMA | 30 | 315.16 | 19.5 | | | |
| GMA | 39 | 160.17 | 49.7 | Solution Not Stable | — | — |
| EOEOEMA | 30 | 202.25 | 30.3 | | | |
| Br-HPPMA | 31 | 315.16 | 20.1 | | | |
| EOEAm | 56 | 143.18 | 50.6 | 81.3 | — | — |
| HEAm | 44 | 115.13 | 49.4 | | | |
| EOEAm | 22 | 143.18 | 26.9 | 27.5 | 1.4650 (35 C) | 57 |
| HEAm | 18 | 115.13 | 27.4 | | | |
| EOEOEMA | 17 | 202.25 | 14.7 | | | |
| EOEMA | 13 | 158.20 | 14.4 | | | |
| Br-HPPMA | 30 | 315.16 | 16.7 | | | |
| EOEAm | 21 | 143.18 | 26.1 | 23.5 | 1.4695 (35 C) | 58 |
| HEAm | 17 | 115.13 | 26.3 | | | |
| EOEOEMA | 17 | 202.25 | 15.0 | | | |
| EOEMA | 13 | 158.20 | 14.6 | | | |
| Br-HPPMA | 32 | 315.16 | 18.1 | | | |
| HEAm | 35 | 115.13 | 51.3 | 36.5 | 1.4560 (35 C) | 67 |
| EOEOEMA | 20 | 202.25 | 16.7 | | | |
| EOEMA | 15 | 158.20 | 16.0 | | | |
| Br-HPPMA | 30 | 315.16 | 16.1 | | | |
| DMA | 25 | 99.13 | 42.2 | 17.8 | 1.4830 (35 C) | 46 |
| EOEOEMA | 25 | 202.25 | 20.7 | | | |
| EOEMA | 20 | 158.20 | 21.2 | | | |
| Br-HPPMA | 30 | 315.16 | 15.9 | | | |
| HEAm | 25 | 115.13 | 38.6 | — | | — |
| EOEOEMA | 25 | 202.25 | 22.0 | | | |

TABLE 1-continued

| Component | Wt % | MW (g/mol) | Mole % | Water Content (%) | RI$_{546nm}$ | Tg (Dry) |
|---|---|---|---|---|---|---|
| EOEMA | 20 | 158.20 | 22.5 | | | |
| Br-HPPMA | 30 | 315.16 | 16.9 | | | |
| DMA | 40 | 99.13 | 62.4 | 40.2 | | |
| EOEOEMA | 30 | 202.25 | 22.9 | | | |
| Br-HPPMA | 30 | 315.16 | 14.7 | | | |
| DMA | 30 | 99.13 | 50.8 | 28.9 | | |
| EOEOEMA | 40 | 202.25 | 33.2 | | | |
| Br-HPPMA | 30 | 315.16 | 16.0 | | | |
| GMA | 35 | 160.17 | 42.9 | | | — |
| DMA | 5 | 99.13 | 9.9 | | | |
| EOEOEMA | 28 | 202.25 | 27.2 | | | |
| Br-HPPMA | 32 | 315.16 | 20.0 | | | |

Example 4

Injection Comparison

A 40/30/30 GMA/EOEOEMA/Br-HPPMA compound of Example 3 and IOL25 were prepared into similar IOLs. Both materials were injected in Medicel 1.6 mm Accuject injectors. The IOLs were loaded exacting the same with the HPMC viscoelastic injected into the tips and chamber of the injector. All of the IOLs were loaded the same way with the leading haptic facing down. More viscoelastic was applied on the top of part and them the injector was closed and after three minutes the IOLs were injected. The amount of force needed to push the part through the injector on a 0-5 scale was reported. The time it took the IOL to unfold after injection was recorded. The temperatures of the saline the IOLs were injected into as well as the room temperature were also recorded.

It was observed that the compound of Example 3 material injected very smooth with minimum force and no damage to the IOL or the injector tip. It was also observed that the IOL25 material injections of the same power IOL, required as much as four times the force to go through the same size injectors. Damage to the IOL25 material IOLs and to the tips of the injectors used were also observed.

TABLE 2

| Injection | HPMC Viscoelastic Dwell Time 3 Minutes | | | | |
|---|---|---|---|---|---|
| tip size: | 1.6 | 1.6 | 1.6 | 1.6 | 1.6 |
| saline temp: | 24 | 24 | 24 | 24 | 24 |
| room temp: | 24 | 24 | 24 | 24 | 24 |
| seconds to open: | 1 | 1 | 1 | 1 | 1 |
| FORCE 0-5 | 1 | 2 | 2 | 2 | 2 |
| tip inspection @ 16X | good** | good** | good** | good** | good** |
| visual inspection @ 16X | good* | good* | good* | good* | good* |

| I25 Injection | HPMC Viscoelastic Dwell Time 3 Minutes | | |
|---|---|---|---|
| tip size: | 1.6 | 1.6 | 1.6 |
| saline temp: | 22 | 22 | 22 |
| room temp: | 21 | 21 | 21 |
| seconds to open: | 1 | 1 | 1 |
| FORCE 0-5 | 4 | 3 | 4 |
| tip inspection @ 16X | slight deformation | good** | good** |
| visual inspection @ 16X | good* | good* | haptic cut |

**No visual defects, deformation, splits or tears on tip
*No visual defects on the optic or haptics As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all sub ratios falling within the broader ratio.

One skilled in the art will also readily recognize that where members are grouped together in a common manner, such as in a Markush group, the present embodiments encompasses not only the entire group listed as a whole, but each member of the group individually and all possible subgroups of the main group. Accordingly, for all purposes, the present embodiments encompass not only the main group, but also the main group absent one or more of the group members. The present embodiments also envisage the explicit exclusion of one or more of any of the group members in the claimed embodiments.

All references, patents and publications disclosed herein are specifically incorporated by reference in their entireties and for all purposes as if fully set forth in their entireties. Unless otherwise specified, "a" or "an" means "one or more".

While preferred embodiments have been illustrated and described, it should be understood that changes and modifications can be made therein in accordance with ordinary skill in the art without departing from the embodiments in its broader aspects as defined in the following claims.

What is claimed is:

1. A hydrophilic intraocular lens comprising at least one copolymer comprising:
    (a) a first monomeric subunit consisting of a polymerized (meth)acrylate group and an aliphatic carbon moiety that is substituted with two hydroxyl substituents,
    (b) a second monomeric subunit different from the first monomeric subunit comprising a polymerized (meth)acrylate group, at least one side group comprising (i) an aryloxy moiety comprising at least one halogen, and (ii) an aliphatic carbon moiety linking the aryloxy moiety with the polymerized (meth)acrylate group, wherein the aliphatic carbon moiety optionally comprises at least one hydroxyl substituent,
    (c) a third monomeric subunit different from the first and second monomeric subunits comprising a polymerized (meth)acrylate group and at least one alkoxyalkoxyalkyl side group, wherein the first monomeric subunit is about 30% to about 50%, by weight of the copolymer composition, the second monomeric subunit is about 20% to about 40%, by weight of the copolymer composition, and the third monomeric subunit is about 20% to about 40%, by weight of the copolymer composition.

2. The hydrophilic intraocular lens of claim 1, wherein the copolymer further comprises a fourth monomeric subunit different from the first, second and third monomeric subunits comprising a polymerized (meth)acrylate group and at least one alkoxyalkyl side group.

3. The hydrophilic intraocular lens of claim 1, wherein the copolymer further comprises monomeric subunits that are crosslinked subunits.

4. The hydrophilic intraocular lens of claim 1, wherein the aryloxy group of the second monomeric subunit comprises a phenoxy group.

5. The hydrophilic intraocular lens of claim 1, wherein the aliphatic carbon moiety of the second monomeric subunit is substituted with one hydroxyl group.

6. The hydrophilic intraocular lens of claim 1, wherein the halogen in the second monomeric subunit is a bromo moiety.

7. The hydrophilic intraocular lens of claim 1, wherein the aliphatic carbon moiety of the second monomeric subunit is a $C_3$ moiety.

8. The hydrophilic intraocular lens of claim 1, wherein the aliphatic carbon moiety of the second monomeric subunit is represented by $CH_2$—CHOH—$CH_2$.

9. The hydrophilic intraocular lens of claim 1, wherein the alkoxyalkoxyalkyl group of the third monomeric subunit is a $C_3$ to $C_{12}$ group.

10. The intraocular lens of claim 1, wherein the alkoxyalkoxyalkyl group of the third monomeric subunit comprises two oxygen atoms.

11. The hydrophilic intraocular lens of claim 1, wherein the alkoxyalkoxyalkyl group of the third monomeric subunit is 2-ethoxyethoxyethyl.

12. The hydrophilic intraocular lens of claim 1, wherein the aliphatic carbon moiety that is substituted with two hydroxyl substituents of the first monomeric subunit includes a $C_2$ to $C_6$ aliphatic carbon moiety.

13. The hydrophilic intraocular lens of claim 1, wherein the first monomeric subunit is polymerized 2,3-dihydroxypropyl methacrylate.

14. The hydrophilic intraocular lens of claim 2, wherein the alkoxyalkyl group of the fourth monomeric subunit is a $C_3$ to $C_{12}$ group.

15. The hydrophilic intraocular lens of claim 2, wherein the alkoxyalkyl group of the fourth monomeric subunit comprises a single oxygen atom.

16. The hydrophilic intraocular lens of claim 2, wherein the alkoxyalkyl group of the fourth monomeric subunit is 2-ethoxyethyl.

17. The hydrophilic intraocular lens of claim 1, wherein the third monomeric subunit comprises polymerized 2-ethoxyethoxyethyl methacrylate and the second monomeric subunit comprises polymerized:

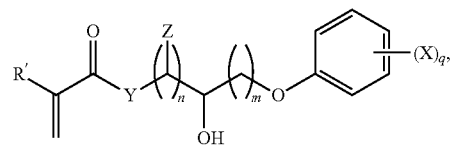

wherein:
R' is methyl;
Y is O;
X is Br;
Z is H;
n is 1;
m is 1; and
q is 1, 2, 3, 4, or 5.

18. The hydrophilic intraocular lens of claim 1, wherein the copolymer further comprises one or more of UV absorbers, initiation agents and/or crosslinking agents.

19. The hydrophilic intraocular lens of claim 1, wherein the copolymer further comprises monomeric subunits that are crosslinked subunits of a trimethacrylate crosslinker.

20. The hydrophilic intraocular lens of claim 1, wherein the copolymer has an equilibrium water content of 20 wt. % or more at 35° C. in isotonic saline.

21. The hydrophilic intraocular lens of claim 1, wherein the lens has a central thickness of up to 1 mm and unfolds in less than or about 1 minute when placed in a saline solution at a temperature of 35° C.

22. The hydrophilic intraocular lens of claim 1, wherein the lens has a central thickness of up to 1 mm and unfolds in 5 to 20 seconds.

23. The hydrophilic intraocular lens of claim 1, wherein the refractive index at 546 nm and 20° C. is about 1.47 to about 1.50.

24. The hydrophilic intraocular lens of claim 1, wherein the lens is capable of being injected through a tube that has an inner diameter of approximately 1.6 mm.

25. The hydrophilic intraocular lens of claim 1, wherein the refractive index at 546 nm and 20° C. is greater than 1.47.

* * * * *